US010773053B2

(12) United States Patent
Ranum et al.

(10) Patent No.: US 10,773,053 B2
(45) Date of Patent: *Sep. 15, 2020

(54) METHODS OF MANUFACTURING A CATHETER HAVING A SENSOR

(71) Applicant: COVIDIEN LP, Mansfield, MA (US)

(72) Inventors: Daniel A. Ranum, Golden Valley, MN (US); Brian T. Stolz, Bloomington, MN (US); Nathan J. Knutson, Long Lake, MN (US); David M. Costello, Delano, MN (US)

(73) Assignee: COVIDIEN LP, Mansfield (*) Notice: Subject to any disclaimer, the term of this patent is extended or adjusted under 35 U.S.C. 154(b) by 291 days.

This patent is subject to a terminal disclaimer.

(21) Appl. No.: 15/879,087

(22) Filed: Jan. 24, 2018

(65) Prior Publication Data

US 2019/0224447 A1    Jul. 25, 2019

(51) Int. Cl.
*A61M 25/00*       (2006.01)
*A61B 5/06*        (2006.01)
(Continued)

(52) U.S. Cl.
CPC ......... *A61M 25/0012* (2013.01); *A61B 1/018* (2013.01); *A61B 1/2676* (2013.01); *A61B 5/065* (2013.01); *A61B 5/6852* (2013.01); *A61M 25/0105* (2013.01); *B21F 7/00* (2013.01); *B21F 15/04* (2013.01); *B21F 17/00* (2013.01); *B21F 45/008* (2013.01); *A61M 2025/0166* (2013.01); *A61M 2025/0175* (2013.01)

(58) Field of Classification Search
CPC ... A61B 1/00133; A61B 1/0052; A61B 1/018; A61B 1/2676; A61B 5/065; A61B 5/6852; A61M 25/0136; A61M 25/0147; A61M 25/1033; A61M 25/0012; A61M 25/0105; A61M 2025/0175; A61M 2025/0166; B21F 7/00; B21F 15/04; B21F 17/00; B21F 45/008
See application file for complete search history.

(56) References Cited

U.S. PATENT DOCUMENTS 4,175,992 A    11/1979  Grawey
5,395,329 A *   3/1995  Fleischhacker ... A61M 25/0147
                                                604/95.04
(Continued)

FOREIGN PATENT DOCUMENTS

CN    104840249 A    8/2015
CN    105615991 A    6/2016
(Continued)

OTHER PUBLICATIONS

International Search Report and Written Opinion, dated Apr. 1, 2019, corresponding to counterpart International Application No. PCT/US2019/014888; 10 total pages.

*Primary Examiner* — Carl J Arbes

(57) ABSTRACT

A method of manufacturing a flexible catheter with a locatable sensor includes simultaneously rotating first and second spools about a common axis, whereby first and second leads of a wire twist together to form a twisted pair of the wire, and rotating a catheter body about a longitudinal axis defined by the catheter body, whereby the twisted pair of the wire wraps about a proximal end portion of the catheter body.

11 Claims, 8 Drawing Sheets

(51) Int. Cl.
  *B21F 45/00*    (2006.01)
  *A61B 1/018*    (2006.01)
  *A61B 1/267*    (2006.01)
  *A61M 25/01*    (2006.01)
  *B21F 15/04*    (2006.01)
  *A61B 5/00*     (2006.01)
  *B21F 7/00*     (2006.01)
  *B21F 17/00*    (2006.01)

(56) References Cited

U.S. PATENT DOCUMENTS

| | | | |
|---|---|---|---|
| 5,462,527 A * | 10/1995 | Stevens-Wright | ............................ A61B 18/1492 600/585 |
| 5,571,085 A * | 11/1996 | Accisano | .......... A61M 25/0136 604/95.01 |
| 5,727,553 A | 3/1998 | Saad | |
| 5,830,222 A | 11/1998 | Makower | |
| 5,954,654 A * | 9/1999 | Eaton | .................. A61B 1/0052 600/459 |
| 6,030,371 A | 2/2000 | Pursley | |
| 6,078,830 A | 6/2000 | Levin et al. | |
| 6,228,032 B1 * | 5/2001 | Eaton | .................. A61B 1/0052 600/463 |
| 6,253,770 B1 | 7/2001 | Acker et al. | |
| 6,869,431 B2 | 3/2005 | Maguire et al. | |
| 7,386,339 B2 | 6/2008 | Strommer et al. | |
| 7,613,493 B2 * | 11/2009 | Mansouri-Ruiz | .... A61B 8/4461 600/407 |
| 7,641,480 B1 * | 1/2010 | Hossack | .................. A61B 8/12 439/335 |
| 7,668,583 B2 | 2/2010 | Fegert et al. | |
| 7,771,416 B2 * | 8/2010 | Spivey | ............... A61B 1/00133 600/106 |
| 8,052,609 B2 * | 11/2011 | Harhen | .................... A61B 8/12 600/136 |
| 8,285,362 B2 | 10/2012 | Dietz et al. | |
| 8,287,453 B2 | 10/2012 | Li et al. | |
| 8,361,066 B2 | 1/2013 | Long et al. | |
| 8,857,304 B2 | 10/2014 | Govari et al. | |
| 9,078,570 B2 | 7/2015 | Parks et al. | |
| 9,125,578 B2 | 9/2015 | Grunwald | |
| 9,144,458 B2 | 9/2015 | Takaoka et al. | |
| 10,105,036 B2 * | 10/2018 | Julian | .................. A61B 1/0053 |
| 2003/0004460 A1 * | 1/2003 | Bedell | ................ A61B 1/00082 604/95.04 |
| 2005/0015044 A1 | 1/2005 | Harttig et al. | |
| 2006/0052664 A1 * | 3/2006 | Julian | .................. A61B 1/0053 600/146 |
| 2006/0235304 A1 * | 10/2006 | Harhen | .................... A61B 8/12 600/459 |
| 2006/0252993 A1 * | 11/2006 | Freed | .................. A61B 1/0052 600/146 |
| 2006/0287700 A1 | 12/2006 | White et al. | |
| 2009/0018566 A1 | 1/2009 | Escudero et al. | |
| 2009/0234328 A1 | 9/2009 | Cox et al. | |
| 2010/0331644 A1 | 12/2010 | Neale et al. | |
| 2012/0149967 A1 | 6/2012 | Ludwin et al. | |
| 2012/0172842 A1 | 7/2012 | Sela et al. | |
| 2012/0265102 A1 | 10/2012 | Leo et al. | |
| 2013/0245433 A1 | 9/2013 | Deladi et al. | |
| 2015/0080858 A1 | 3/2015 | Moss | |
| 2015/0374435 A1 | 12/2015 | Cao et al. | |
| 2016/0184013 A1 | 6/2016 | Brannan et al. | |
| 2017/0079546 A1 | 3/2017 | Costello et al. | |

FOREIGN PATENT DOCUMENTS

| | | |
|---|---|---|
| EP | 421650 A1 | 4/1991 |
| JP | 2011143072 A | 7/2011 |
| WO | 2015160064 A1 | 10/2015 |

* cited by examiner

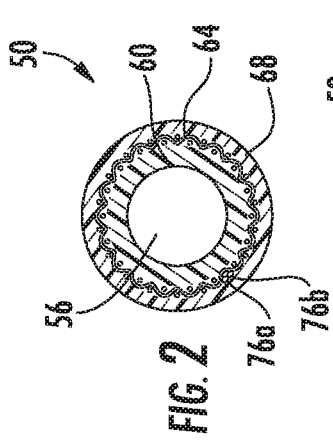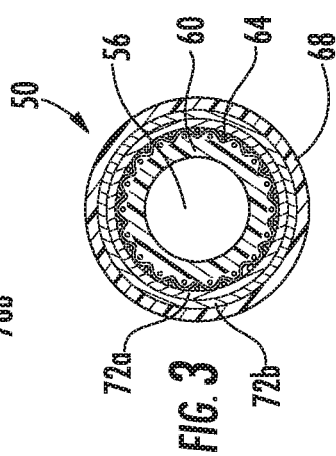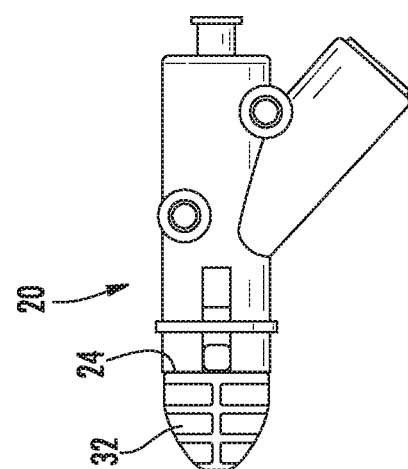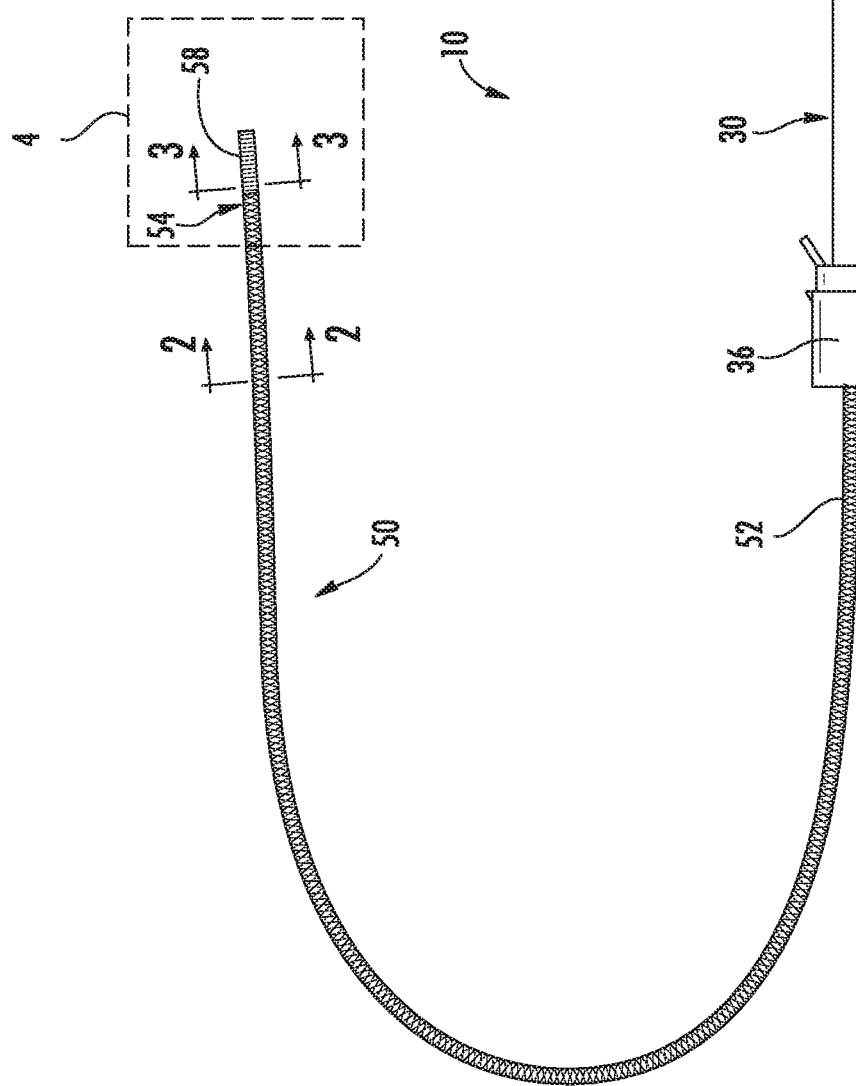

METHODS OF MANUFACTURING A CATHETER HAVING A SENSOR

BACKGROUND

1. Technical Field

The present disclosure relates to elongated catheters and, more specifically, to methods of manufacturing elongated catheters having a sensor and an extended working channel.

2. Discussion of Related Art

A common interventional procedure in the field of pulmonary medicine is bronchoscopy, in which a bronchoscope is inserted into the airways through the patient's nose or mouth. The structure of a bronchoscope generally includes a long, thin, flexible tube that typically contains three elements: an illumination assembly for illuminating the region distal to the bronchoscope's tip via an optical fiber connected to an external light source; an imaging assembly for delivering back a video image from the bronchoscope's distal tip; and a lumen or working channel through which instruments may be inserted, including, but not limited to, placement instruments (e.g., guide wires), diagnostic instruments (e.g., biopsy tools) and therapeutic instruments (e.g., treatment catheters or laser, cryogenic, radio frequency, or microwave tissue treatment probes).

During some procedures (e.g., microwave ablation and biopsy), a catheter having an extended working channel may be inserted through a working channel to enable navigation to sites that are typically too remote, or have luminal diameters too small, for the bronchoscope. The catheter may have a locatable sensor at its distal end to assist in guiding the catheter to targeted tissue. When the distal end of the catheter is positioned adjacent targeted tissue, an instrument may be inserted through the extended working channel of the catheter to perform a procedure on the targeted tissue (e.g., perform a biopsy or ablation of the targeted tissue).

Presently, the sensor on the catheter is fabricated using a plurality of discreet wires that require a metal bonding connection. Since the distal end of the catheter is subjected to bending forces during use, the sensor and its connections experience strain.

Accordingly, there is a need for catheters with a locatable sensor having a longer useful life.

SUMMARY

In an aspect of the present disclosure, a method of manufacturing a flexible catheter with a locatable sensor is provided. The method includes non-rotatably coupling a first spool to a first portion of a spool carrier. A first portion of a wire is wrapped about the first spool and a second portion of the wire is wrapped about a second spool. The spool carrier is non-rotatably coupled to a catheter body, and the spool carrier is rotated with the catheter body, thereby wrapping a second portion of the wire about a distal end portion of the catheter body to form a first wrapping layer. The first spool and second spools are coupled to a drive motor. The drive motor is activated to rotate the first and second spools about a common axis, whereby first and second leads of the wire twist together to form a twisted pair of the wire. Simultaneously with the activation of the drive motor, the catheter body rotates about a longitudinal axis defined by the catheter body, whereby the twisted pair of the wire wraps about a proximal end portion of the catheter body.

In some methods, the second portion of the wire may unravel from the second spool as the spool carrier is rotated.

Some methods may further include forming a second wrapping layer over the first wrapping layer with the second portion of the wire.

Some methods may further include axially moving the catheter body relative to the first and second spools while the drive motor is activated and the catheter body is rotated. Some methods may alternatively include axially moving the first and second spools relative to the catheter body while the drive motor is activated and the catheter body is rotated.

In some methods, the first and second spools may rotate about their respective longitudinal axes in response to the rotation of the catheter body.

In some methods, non-rotatably coupling the spool carrier to the catheter body may include capturing the catheter body within a channel defined through a length of an elongate body of the spool carrier. The first portion of the spool carrier may extend outwardly from the elongate body.

In some methods, non-rotatably coupling the spool carrier to the catheter body may further include fixing the elongate body of the spool carrier to the catheter body.

In some methods, the catheter body may include at least an inner liner. The inner liner may be disposed about a rotatable mandrel.

In some methods, the spool carrier may be rotated in response to a rotation of the mandrel.

Some methods may further include routing the wire through a wire guide, and positioning the wire across an outer surface of the catheter body prior to rotating the spool carrier.

Some methods may further include applying an adhesive to a plurality of locations of the twisted pair of the wire.

Further, to the extent consistent, any of the aspects described herein may be used in conjunction with any or all of the other aspects described herein.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Various aspects of the present disclosure are described hereinbelow with reference to the drawings, which are incorporated in and constitute a part of this specification, wherein:

FIG. 1 is a side view of a catheter assembly provided in accordance with the present disclosure;

FIG. 2 is a cross-sectional view of the catheter assembly of FIG. 1 taken along the section line 2-2 of FIG. 1;

FIG. 3 is a cross-sectional view of the catheter assembly of FIG. 1 taken along the section line 3-3 of FIG. 1;

DETAILED DESCRIPTION

Figure 4:
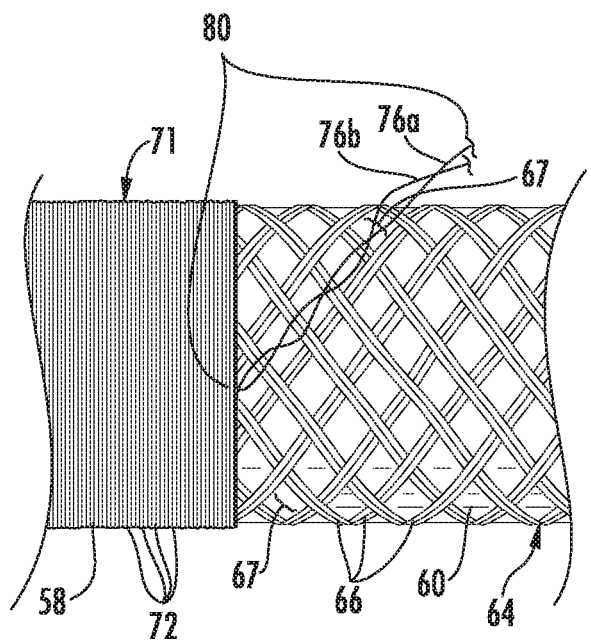
FIG. 4 is an enlarged view of the area of detail designated "4" in FIG. 1.

This disclosure relates generally to a method of forming a wire sensor on a catheter. The sensor is used for locating the distal end portion of an extended working channel ("EWC") of the catheter within the anatomy of a patient. A spool carrier assists in forming both a sensor on a distal end portion of the catheter and a twisted pair that extends proximally from the sensor along a proximal end portion of the catheter and connects to a flexible circuit pad.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Referring now to FIG. 1, a catheter assembly 10 is provided in accordance with the present disclosure and includes a handle assembly 20, a telescopic channel 30, and an elongated catheter body 50 having a proximal end portion 52 and a distal end portion 54. The handle assembly 20 is coupled to the proximal end portion 52 of the catheter body 50 to permit a clinician to manipulate the catheter assembly 10.

The telescopic channel 30 is positioned between the handle assembly 20 and the proximal end portion 52 of the catheter body 50 to provide lateral support for the catheter body 50. The telescopic channel 30 includes a proximal or first end portion 32 that is coupled to a distal end portion 24 of the handle assembly 20 and a distal or second end portion 36 that is configured to couple the catheter assembly 10 to a bronchoscope (not shown). The telescopic channel 30 includes an extendable body portion 34 between the first and second end portions 32, 36 that is expandable along a longitudinal axis and substantially rigid transverse to the longitudinal axis. The extendable body portion 34 allows the first end portion 32 to translate along and rotate about the longitudinal axis relative to the second end portion 36. When the first end portion 32 is coupled to the handle assembly 20, the proximal end portion 52 of the catheter body 50 translates and rotates with the first end portion 32 of the telescopic channel 30.

With additional reference to FIGS. 2 and 3, the catheter body 50 defines an EWC 56 along a length thereof. The EWC 56 allows instruments (not shown) to be inserted through the catheter body 50 to treat targeted tissue adjacent the distal end portion 54 of the catheter body 50. The catheter body 50 includes an inner liner 60, a braid 64, and an outer coating 68. The inner liner 60 defines the EWC 56 that passes entirely through the catheter body 50. It is contemplated that the catheter body 50 may be constructed without the inner liner 60 such that the braid 64 defines the EWC 56.

With additional reference to FIG. 4, as described in greater detail below, a sensor 58 is formed of one continuous wire 71 wrapped over the braid 64 and covered by the outer coating 68 to form the sensor 58. The wire 71 includes leads 76a, 76b that are twisted together to form a twisted pair 80 that is coiled about the braid 64 along the proximal end portion 52 of the catheter body 50. It will be appreciated that while the portions of the wire 71 (e.g., the leads 76a, 76b) are discussed individually herein, the wire 71 is monolithically formed (i.e., the wire 71 is one continuous wire without any solder joints between different portions thereof). By forming the sensor 58 from one continuous monolithic wire 71, the useful life of the sensor 58, and thus the catheter body 50, is increased.

The inner liner 60 and the outer coating 68 are formed from polymer tubes, as detailed below, which are made from of a reflowable polymer material (e.g., thermoplastic polymers or polytetrafluoroethylene (PTFE)) which may bond to the braid 64, the wire 71, and to one another. The braid 64 is constructed of a mesh of between 16 and 32 of similar or varying material cords woven together (e.g., stainless steel, polyethylene naphthalate (PEN), polyethylene terephthalate (PET), and/or insulated electrical wire). The wire 71 is a solid core magnetic wire with a thin dielectric coating (e.g., a copper wire with a polyimide coating).

Figure 5:
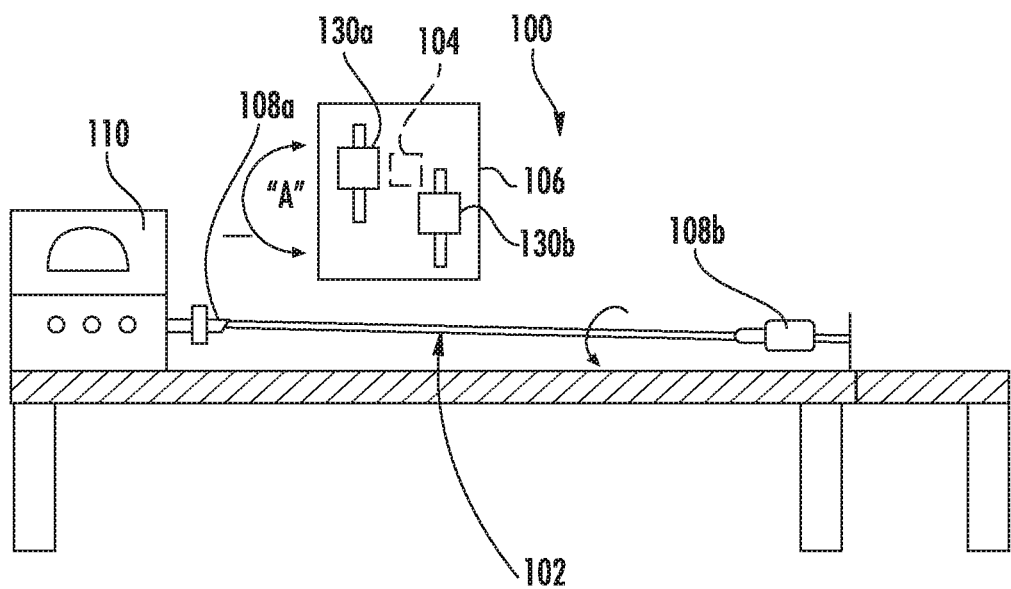
FIG. 5. is a side view of a coil winding station for manufacturing a catheter body and sensor of the catheter assembly of FIG. 1.
Figure 6:
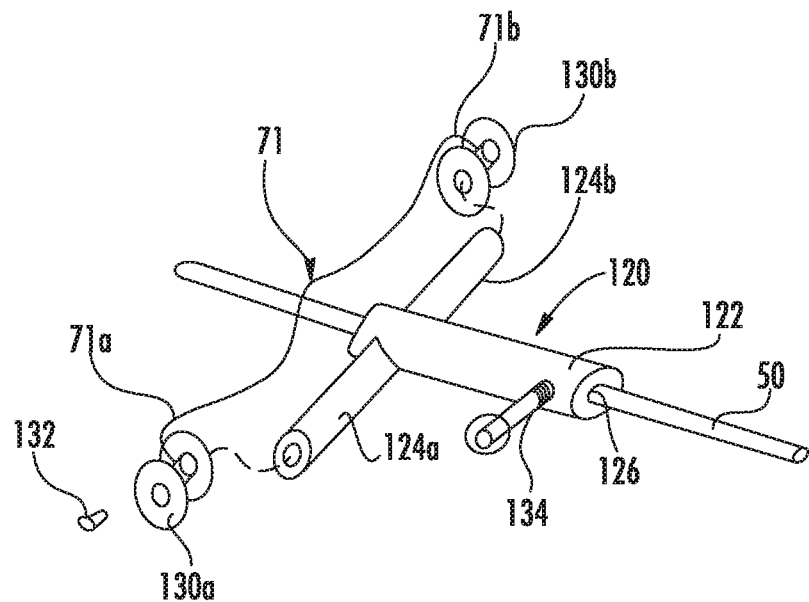
FIG. 6 is a perspective view of a spool carrier and a pair of spools having a wire connected thereto for forming the sensor of the catheter assembly of FIG. 1.

With reference to FIGS. 5 and 6, a coil winding station 100 and a spool carrier 120 are utilized to form the catheter body 50 with the sensor 58. The coil winding station 100 generally includes a mandrel 102, a drive motor 104 operably coupled to a rotatable hub 106, and a control system 110 (e.g., a computer) for operating the components of the coil winding station 100. The hub 106 is configured to rotatably support first and second spools 130a, 130b thereon. The hub 106 rotates, in the direction indicated by arrow "A," in response to an activation of the drive motor 104. A first end of the mandrel 102 is secured to a head stock chuck 108a, and a second end of the mandrel 102 is secured to a tail stock chuck 108b. The mandrel 102 is rotatable about its longitudinal axis via rotation of the head and/or tail stock chucks 108a, 108b.

FIG. 6 depicts the spool carrier 120, which includes an elongate body 122 and a pair of portions or arms 124a, 124b extending perpendicularly from the elongate body 122. In embodiments, the spool carrier 120 may only have one arm 124a or 124b. The elongate body 122 defines a channel 126 extending through a length thereof. The channel 126 is configured for receipt of the mandrel 102 or the catheter body 50. The spool carrier 120 has a fastener, such as, for example, a screw 134 to secure the elongate body 122 to the catheter body 50 such that rotation of the catheter body 50 results in rotation of the spool carrier 120. In embodiments, instead of using screw 134, the elongate body 122 may be secured to the catheter body 50 using magnets, wire clips, detents, pins, adhesives, hook and loop fasteners, or the like. The arms 124a, 124b of the spool carrier 120 are disposed on opposite sides of the elongate body 122 and are each configured to couple to a respective spool 130a, 130b, such as, for example, bobbins.

With reference to FIGS. 2-5, a method of manufacturing the catheter body 50 will now be described. Initially, the inner liner 60 is slid over the mandrel 102, which provides rigidity to the flexible components of the catheter body 50 while the catheter body 50 is being assembled. The inner liner 60 has an inner diameter substantially equal to but slightly larger than an outer diameter of the mandrel 102 and has a length substantially equal to a length of the mandrel 102. The mandrel 102 may be coated with a PTFE coating to assist in sliding the inner liner 60 over the mandrel 102 and to prevent the inner liner 60 from bonding to the mandrel 102. The outer diameter of the mandrel 102 is substantially equal to a desired diameter of the EWC 56 and the length of the mandrel 102 is longer than a final desired length of the catheter body 50. The mandrel 102 may have a diameter in a range of about 0.050 to about 0.100 inches (e.g., about 0.090 inches) and have a length in a range of about 30 to about 90 inches (e.g., about 62 inches).

The braid 64 of the catheter body 50 is formed over the inner liner 60 with portions of the braid 64 extending beyond the ends of the mandrel 102 such that the mandrel 102 and the inner liner 60 may be completely within the braid 64. The braid 64 is formed by helically weaving cords 66 of material over a cylinder (e.g., the inner liner 60 and the mandrel 102). The cords 66 define channels 67 therebetween that follow the helical pattern of the cords 66. The pitch of the cords 66 may be in a range of about 0.125 to about 0.225 (e.g., about 0.177). The braid 64 may compress the inner liner 60 over the mandrel 102. The braid 64 may have an outer diameter in a range of about 0.052 to about 0.102 inches (e.g., 0.092 inches). It is contemplated that the inner liner 60, the braid 64, and the mandrel 102 may be supplied as a preassembled unit.

With reference to FIGS. 7-18, a method of forming the sensor 58 on the catheter body 50 utilizing the coil winding station 100 and the spool carrier 120 will now be described. Formation of the sensor 58 generally includes wrapping the wire 71 over the braid 64 of the catheter body 50 to form two wrapping layers 72a, 72b (FIG. 3) over the distal end portion 54 of the catheter body 50, and then twisting together leads 76a, 76b of the wire 71 while wrapping the twisted leads 76a, 76b around the proximal end portion 52 of the catheter body 50. In some methods, the wire 71 may be wrapped over the inner liner 60, the PTFE liner, the outer coating 68, or any other suitable portion of the catheter body 50.

Figure 7:
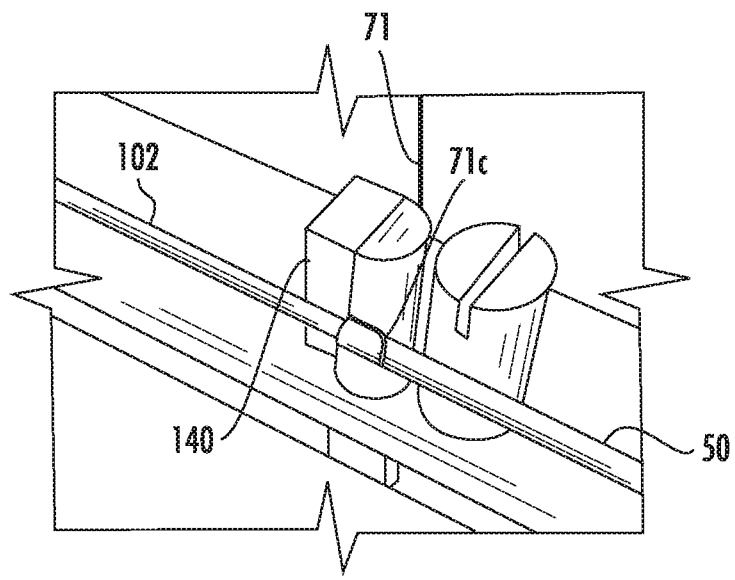
FIG. 7 is a perspective view, illustrating a wire laid over the catheter body and inserted into a wire guide.
Figure 8:
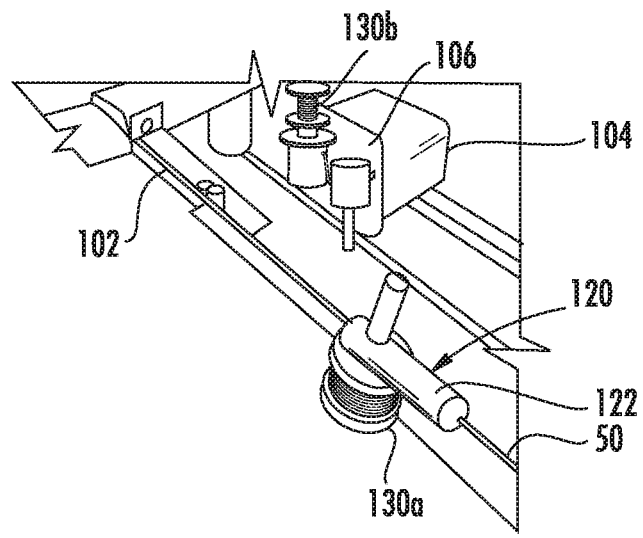
FIG. 8 is a perspective view, illustrating the spool carrier of FIG. 6 coupled to the catheter body.

With reference to FIGS. 6-8, the wire 71 has a first end portion 71a wrapped about the first spool, and a second end portion 71b wrapped about the second spool 130b. The first spool 130a is positioned on the first arm 124a of the spool carrier 120, and the second spool 130b is positioned on the hub 106 of the coil winding station 100. The first spool 130a is prevented from rotating relative to the first arm 124a of the spool carrier 120 via a fastener 132 (e.g., a set screw or a thumb screw). The second spool 130b is free to rotate relative to the hub 106 about a longitudinal axis defined by the second spool 130b.

The inner liner 60 with braid 64 of the catheter body 50 is disposed on the mandrel 102 of the coil winding station 100. An intermediate portion 71c of the wire 71 is laid transversely over the distal end portion 54 of the catheter body 50 (e.g., the inner liner 60 or PTFE coating) and routed through a wire guide 140 of the coil winding station 100, as shown in FIG. 7. The intermediate portion 71c of the wire 71 is adhered to the distal end portion 54 of the catheter body 50 using a UV cure adhesive or a piece of tape. In embodiments, the intermediate portion 71c of the wire 71 may be secured to the distal end portion 54 of the catheter body 50 via any suitable fastening mechanism. For example, the wire 71 may include a bondable coating that is heat or solvent activated.

The catheter body 50 is fixed to the mandrel 102 between the head and tail stocks 108a, 108b. The catheter body 50 is captured in the channel 126 of the spool carrier 120 to non-rotatably couple the spool carrier 120 with the catheter body 50 and mandrel 102. In embodiments, the spool carrier 120 may be non-rotatably coupled directly to the mandrel 102 rather than the catheter body 50.

Figure 9:
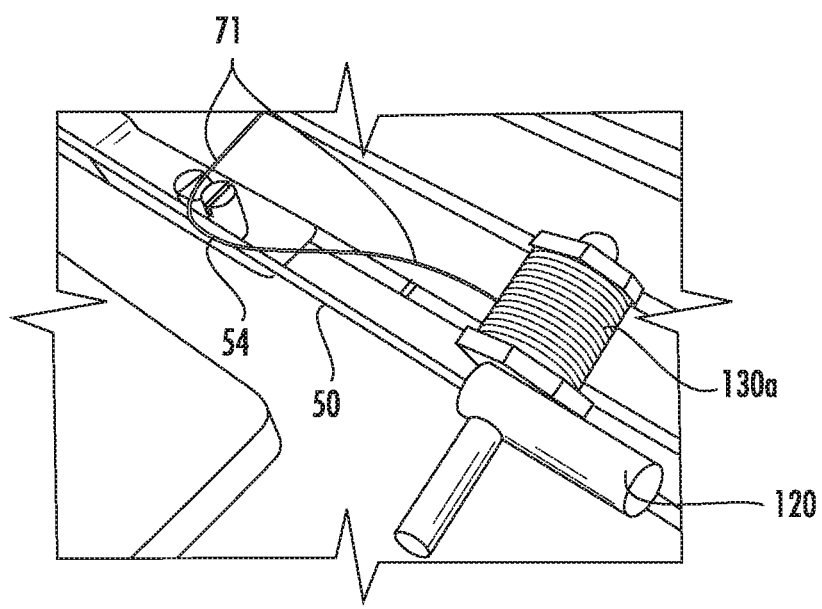
FIG. 9 is a top, perspective view, illustrating the spool carrier after having been rotated to form a first coil in the wire about the catheter body.
Figure 10:
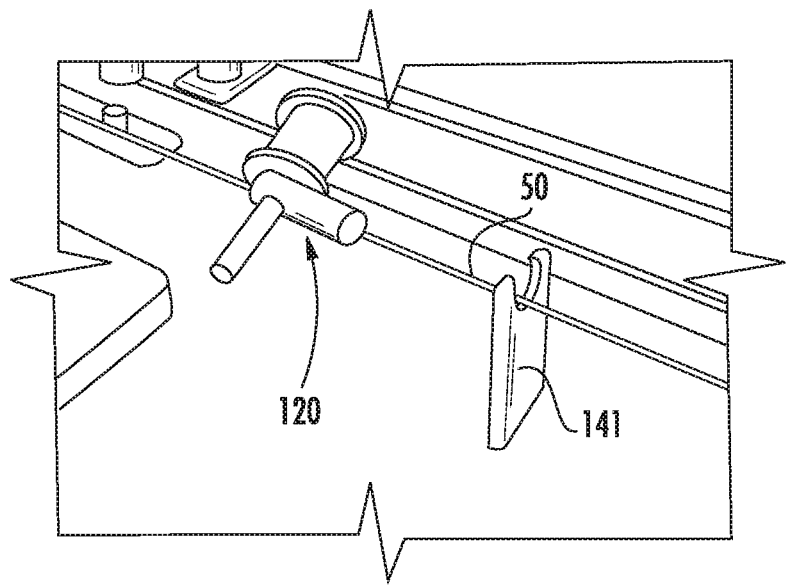
FIG. 10 is a side, perspective view, illustrating a mandrel of the coil winding station of FIG. 5 disposed within a mandrel guide.

With the intermediate portion 71c of the wire 71 fixed to the catheter body 50, the spool carrier 120 is rotated approximately ½ turn to wrap the wire 71 once about the catheter body 50, as shown in FIG. 9. The mandrel 102 is positioned in a mandrel guide 141 to support the mandrel 102, as shown in FIG. 10. The mandrel 102 is rotated at a predetermined rate, and in turn, the catheter body 50 rotates about a longitudinal axis defined by the catheter body 50. Since the spool carrier 120 is non-rotatably coupled to the catheter body 50, the spool carrier 120 rotates with the catheter body 50. Rotation of the spool carrier 120 pulls the second end portion 71b of the wire 71 to unravel the second end portion of 71b of the wire 71 from the second spool 130b.

Figure 11:
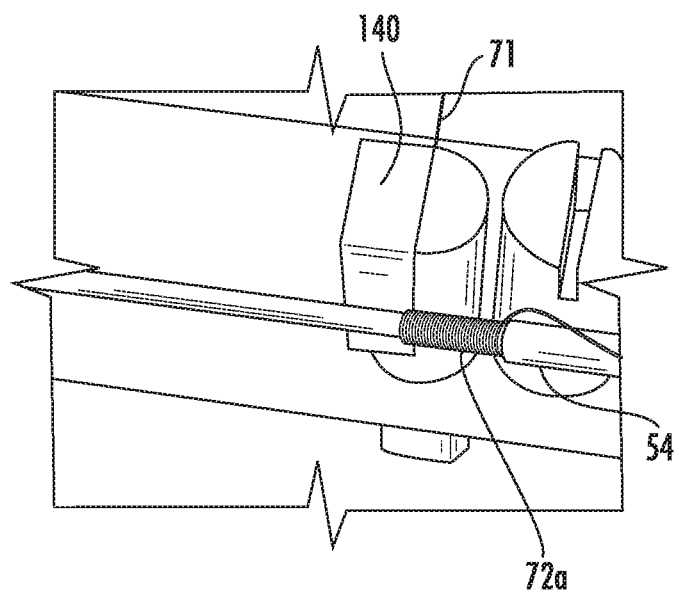
FIG. 11 is a top, perspective view, illustrating the catheter body having a first wrapping layer of the wire formed thereabout.

Simultaneously with the rotation of the spool carrier 120, the catheter body 50 is moved proximally relative to the second spool 130b at a predetermined rate, whereby the second end portion 71b of the wire 71 wraps about the distal end portion 54 of the catheter body 50 in a distal direction forming a first wrapping layer 72a, as shown in FIG. 11. In some embodiments, instead of the catheter body 50 being moved axially relative to the second spool 130b, the second spool 130b is moved axially relative to the catheter body 50.

Upon the first wrapping layer 72a achieving a suitable length on the distal end portion 54 of the catheter body 50, a piece of tape (e.g., cellophane tape) or adhesive is applied to the inner liner 60 distal to the first wrapping layer 72a at a distance equal to approximately 1 or 2 diameters of the first wrapping layer 72a. The catheter body 50 is moved distally at the predetermined rate, or in some embodiments another predetermined rate, to form a second wrapping layer 72b (FIGS. 3 and 12) over the first wrapping layer 72a.

Each of the first and second wrapping layers 72a, 72b may include a range of about 25 to about 200 individual wraps or loops 72 (e.g., about 100 individual wraps) of the wire 71. The number of wraps 72 in the first wrapping layer 72a may be substantially equal to the number of wraps 72 in the second wrapping layer 72b. As shown, the sensor 58 includes two wrapping layers 72a, 72b; however, it is contemplated that the sensor 58 may include a single wrapping layer or may include more than two wrapping layers. The number of wrapping layers of the wire 71 is proportional to signal strength of the sensor 58 (i.e., as the number of wrapping layers increases, the signal strength of the sensor 58 increases). As the number of wrapping layers is increased, the flexibility of the catheter body 50 in the area of the wrapping layers is reduced and the diameter of the catheter body 50 in the area of the wrapping layers is increased.

The total length of the wrapping layers 72a, 72b is in a range of about 0.04 to about 0.36 inches (e.g., about 0.18 inches). As the total length of the wrapping layers 72a, 72b is increased, the flexibility of the catheter body 50 in the area of the wrapping layers is reduced. Thus, the number wrapping layers, the length of the wrapping layers, and the total number of wrapping layers is a compromise between the signal strength of the sensor 58 and the flexibility and size of the catheter body 50.

In embodiments, a support tube or layer may be positioned over the braid 64 before the wire 71 is wrapped over the braid 64 to form the wrapping layers 72a, 72b of the sensor 58. The support layer may be a ferro-metallic tube or a powder with resin that is configured to strengthen or support the sensor 58 to prevent the sensor 58 from deforming when used. The support layer may increase the signal strength of the sensor 58 such that the length and/or number of wrapping layers required to achieve a desired signal strength for the sensor 58 may be reduced.

Figure 12:
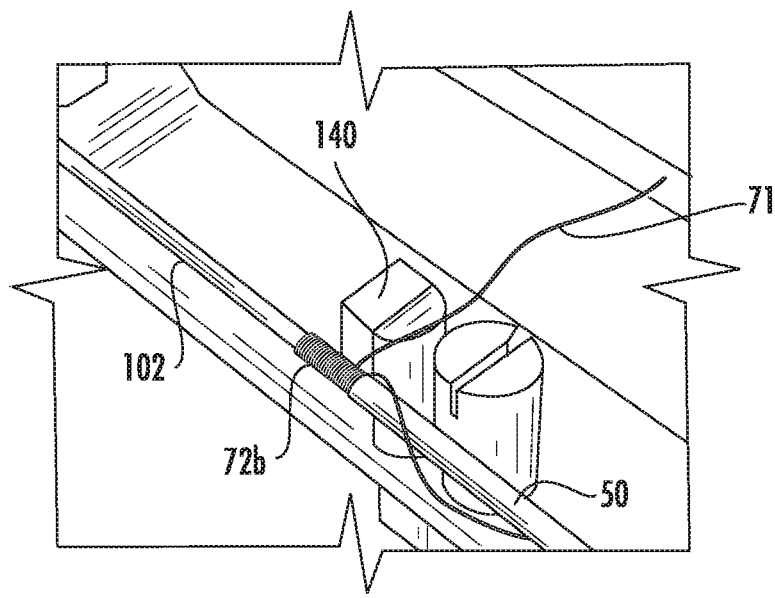
FIG. 12 is a perspective view, illustrating the wire removed from the wire guide.
Figure 13:
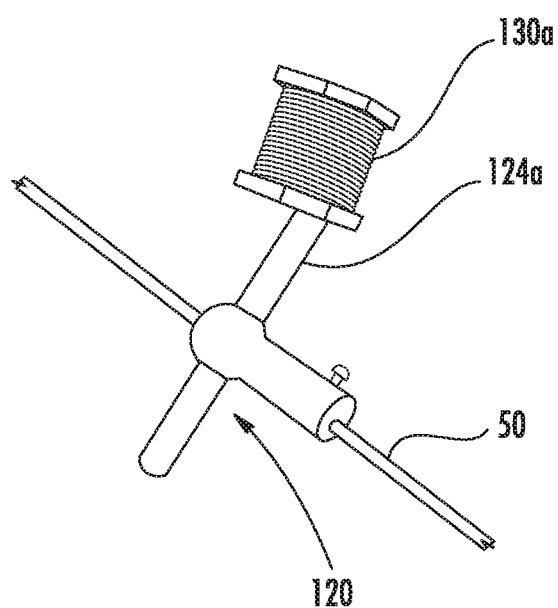
FIG. 13 is a perspective view, illustrating the removal of the spool carrier from the catheter body and the removal of the first spool from the spool carrier.
Figure 14:
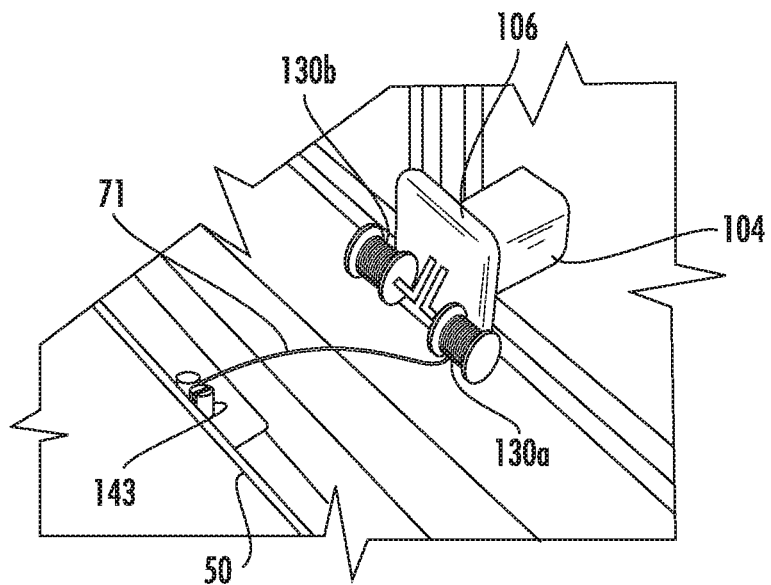
FIG. 14 is a top, perspective view, illustrating the first and second spools coupled to a hub of the coil winding station of FIG. 5.
Figure 15:
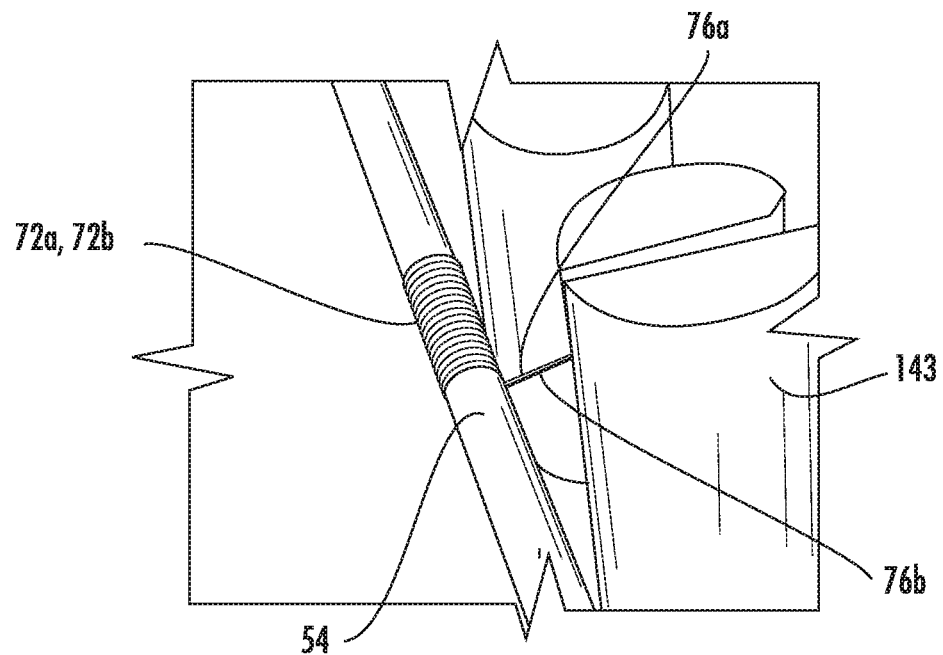
FIG. 15 is a rear, perspective view, illustrating lead lines of the wire being positioned in a twisting guide.

Upon forming the first and second wrapping layers 72a, 72b, adhesive is applied to the entire length or substantially the entire length of the wrapping layers 72a, 72b to secure the wire 71 to the distal end portion 54 of the catheter body 50. As shown in FIG. 12, the wire 71 is removed from the wire guide 140, and as shown in FIG. 13, the first spool 130a is removed from the spool carrier 120, and the spool carrier 120 is detached from the catheter body 50. The first spool 130a is operably coupled to the hub 106, adjacent the second spool 130b, as shown in FIG. 14. As shown in FIG. 15, the lead wires 76a, 76b are positioned in a twisting guide 143 of the coil winding station 100 and aligned with one another so as to extend from the same location of the catheter body 50.

The drive motor 104 is activated to rotate the hub 106 on which the first and second spools 130a, 130b are coupled, and in turn, the first and second spools 130a, 130b rotate about a common axis defined by the drive motor 104. As the spools 130a, 130b rotate about the common axis, the first and second leads 76a, 76b of the wire 71, which extend between the first and second spools 130a, 130b and the wrapping layers 72a, 72b, twist together to form a twisted pair 80 (FIG. 4) of the wire 71. The hub 106 is rotated a predetermined number of turns to yield a suitable number of wire twists per inch along the length of the twisted pair 80 of the wire 71. The leads 76a, 76b may be twisted together in a range of about 5 to about 15 twists per inch (e.g., about 10 twists per inch) of the wire 71. Forming a twisted pair 80 reduces or eliminates a signal from being generated by the wire 71 along the length of the braid 64 (i.e., utilizing the constructive interference to minimize the signal generated).

Simultaneously with the rotation of the hub 106 by the drive motor 104, the catheter body 50 is rotated about its longitudinal axis, thereby exerting a proximally-oriented pulling force on the ends of the first and second leads 76a, 76b. The pulling force exerted on the leads 76a, 76b by the rotation of the catheter body 50 drives a rotation of the first and second spools 130a, 130b about their respective longitudinal axes and relative to the hub 106. Rotation of the first and second spools 130a, 130b about their respective axes allows the leads 76a, 76b to unravel therefrom, causing the twisted pair 80 to wrap around the catheter body 50. In this way, the twisted pair 80 of the wire 71 is coiled about the proximal end portion 52 of the catheter body 50 as the twisted pair 80 is forming. As can be appreciated, there is a delay (e.g., for approximately 1 second) between the start of rotation of the hub 106 and the start of rotation of the catheter body 50.

Figure 16:
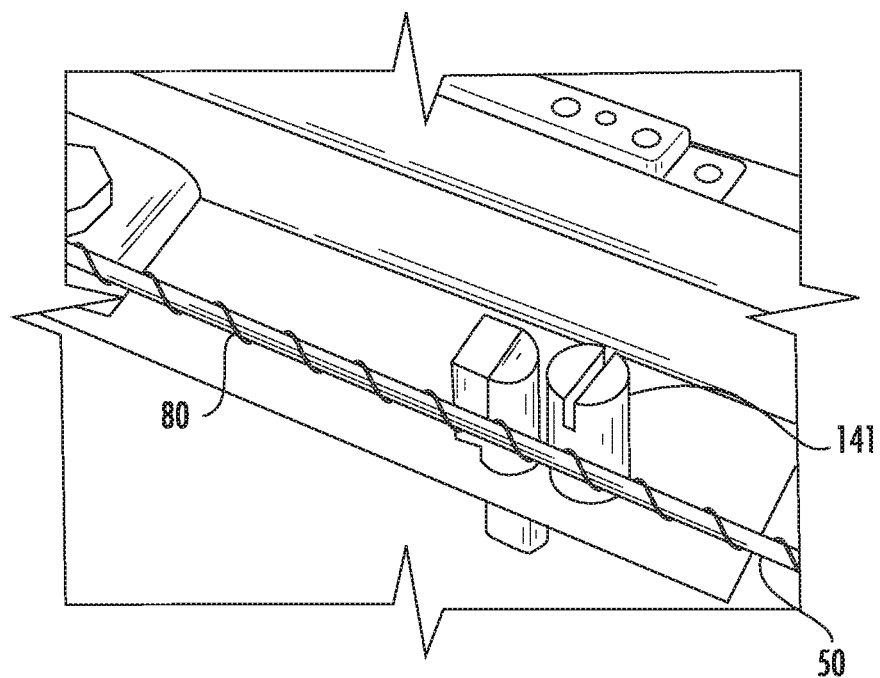
FIG. 16 is a side, perspective view, illustrating an application of adhesive to portions of the wire.

Simultaneously with the rotation of the hub 106 and the rotation of the catheter body 50, the hub 106 with the spools 130a, 130b are moved axially along a track (not shown) relative to the catheter body 50. By axially moving the hub 106 relative to the catheter body 50 as the catheter body rotates, the coil of wire 71 that forms about the catheter body 50 assumes a helical pattern about the proximal end portion 52 of the catheter body 50 along its length, as shown in FIG. 16. The helical pattern of the coil has a predetermined pitch based on the ratio of the rate of rotation and axial movement of the catheter body 50. In some embodiments, instead of axially moving the hub 106 axially relative to the catheter body 50, the catheter body 50 may be axially moved relative to the hub 106/first and second spools 130a, 130b.

Upon coiling the twisted pair 80 of the wire 71 about the catheter body 50, the twisted pair 80 may be adhered to the catheter body 50 using an adhesive, such as, for example, a cyanoacrylate adhesive, applied to a plurality of locations along the length of the catheter body 50, as shown in FIG. 16. After the twisted pair 80 of the wire 71 is formed, the ends of the leads 76a, 76b are severed from the remaining portions of the wire 71 wrapped about the first and second spools 130a, 130b. With the twisted pair 80 coiled about the braid 64 of the catheter body 50, a cover (e.g., a polyamide cover) may be applied over the twisted pair 80.

After formation of the sensor 58 and coiling the twisted pair 80 about the catheter body 50, the outer coating 68 of the catheter body 50 may be slid over or applied to the braid 64 until a proximal end of the outer coating 68 is adjacent to the proximal ends of the twisted pair of leads 76a, 76b. The outer coating 68 may be a polymer tube which is then covered by heat shrink to melt or reflow the polymer such that the outer coating 68 reflows or bonds to the braid 64. In addition, when the outer coating 68 is reflowed, the inner liner 60 within the outer coating 68 may be reflowed to bond with the braid 64 and the outer coating 68. The proximal end of the leads 76a, 76b may be electrically connected (e.g., via solder) to a flexible circuit pad (not shown) to connect to the sensor 58. Other metal bonds may be used to connect leads 76a, 76b to the sensor 58, such as, for example, brazing, swaging, or an ultrasonic/laser/resistance weld.

Forming the wrapping layers 72a, 72b of the sensor 58 and the twisted pair 80 with a single continuous wire 71 increases the service life of the catheter body 50 by eliminating the need for a connection (e.g., a soldered connection) between the wrapping layers 72a, 72b and each of the twisted pair of leads 76a, 76b.

In some embodiments, the wrapping layers 72a, 72b of the sensor 58 and the twisted pair 80 may be preformed apart from the catheter body 50 and then positioned or loaded over the catheter body 50, e.g., the braid 64 or the inner liner 60 of the catheter body 50. In another embodiment, the wrapping layers 72a, 72b of the sensor 58 may be preformed and then loaded over the braid 64 of the catheter body 50, followed by wrapping the twisted pair 80 about the braid 64 using one of the methods detailed above.

For a more detailed description of the construction of various components of the catheter assembly 10, reference may be made to U.S. patent application Ser. No. 15/228,321, filed on Aug. 4, 2016, the entire contents of which are incorporated by reference herein.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A method of manufacturing a flexible catheter with a locatable sensor, the method comprising:
   non-rotatably coupling a first spool to a first portion of a spool carrier, a first portion of a wire being wrapped about the first spool and a second portion of the wire being wrapped about a second spool;
   non-rotatably coupling the spool carrier to a catheter body;
   rotating the spool carrier with the catheter body, thereby wrapping the second portion of the wire about a distal end portion of the catheter body to form a first wrapping layer;
   coupling the first spool and the second spool to a drive motor; and
   simultaneously:
      activating the drive motor to rotate the first and second spools about a common axis, whereby first and second leads of the wire twist together to form a twisted pair of the wire; and
      rotating the catheter body about a longitudinal axis defined by the catheter body, whereby the twisted pair of the wire wraps about a proximal end portion of the catheter body.

2. The method according to claim 1, wherein the second portion of the wire unravels from the second spool as the spool carrier is rotated.

3. The method according to claim 1, further comprising forming a second wrapping layer over the first wrapping layer with the second portion of the wire.

4. The method according to claim 1, further comprising:
   axially moving the catheter body relative to the first and second spools while the drive motor is activated and the catheter body is rotated; or
   axially moving the first and second spools relative to the catheter body while the drive motor is activated and the catheter body is rotated.

5. The method according to claim 4, wherein the first and second spools rotate about their respective longitudinal axes in response to the rotation of the catheter body.

6. The method according to claim 1, wherein non-rotatably coupling the spool carrier to the catheter body includes capturing the catheter body within a channel defined through a length of an elongate body of the spool carrier, the first portion of the spool carrier extending outwardly from the elongate body.

7. The method according to claim 6, wherein non-rotatably coupling the spool carrier to the catheter body further includes fixing the elongate body of the spool carrier to the catheter body.

8. The method according to claim 1, wherein the catheter body includes at least an inner liner, the inner liner disposed about a rotatable mandrel.

9. The method according to claim 8, wherein the spool carrier is rotated in response to a rotation of the mandrel.

10. The method according to claim 1, further comprising:
    routing the wire through a wire guide; and
    positioning the wire across an outer surface of the catheter body prior to rotating the spool carrier.

11. The method according to claim 1, further comprising applying an adhesive to a plurality of locations of the twisted pair of the wire.

* * * * *